Figure 1:
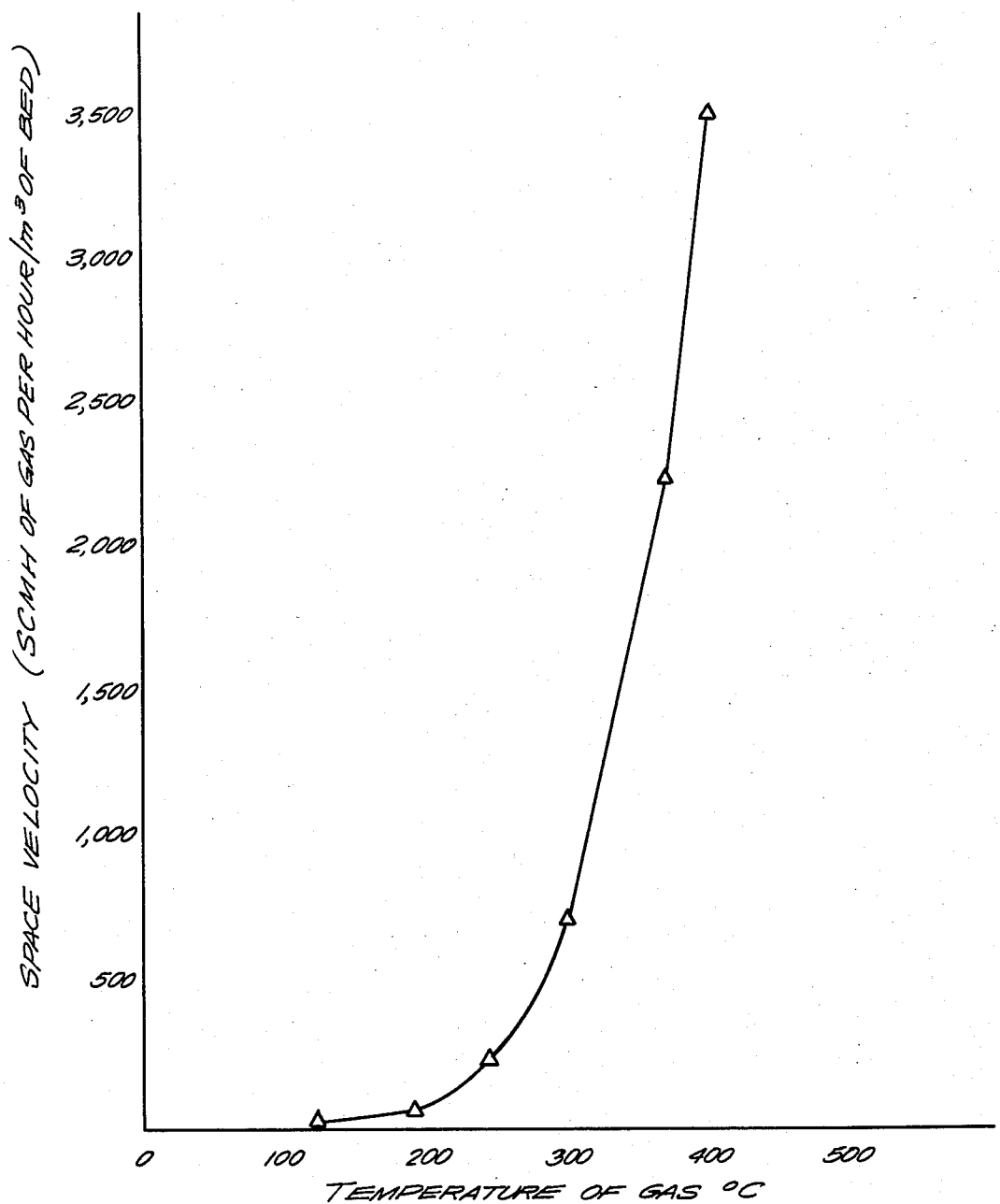

United States Patent [19]

Villarreal-Treviño et al.

[11] Patent Number: 4,608,240

[45] Date of Patent: Aug. 26, 1986

[54] METHOD FOR THE DESULFURIZATION OF HYDROCARBON GAS

[75] Inventors: Juan A. Villarreal-Treviño, San Nicolás de los Garza; Eugenio Zendejas-Martinez; Hector Lopez-Ramos, both of Monterrey, all of Mexico

[73] Assignee: Hylsa, S.A., Monterrey, Mexico

[21] Appl. No.: 549,228

[22] Filed: Nov. 4, 1983

[51] Int. Cl.⁴ .............................................. B01D 53/34
[52] U.S. Cl. ..................................... 423/230; 423/244
[58] Field of Search .................. 423/231, 244 R, 230, 423/561 R, 648 R

[56] References Cited

U.S. PATENT DOCUMENTS

| | | | |
|---|---|---|---|
| 1,317,583 | 9/1919 | Leamon | 423/244 |
| 1,799,359 | 4/1931 | Edmonds | 423/242 |
| 1,815,846 | 7/1931 | Joseph | 423/230 |
| 1,822,293 | 9/1931 | Joseph | 423/230 |
| 1,947,776 | 2/1934 | Huff | 423/230 |
| 1,984,727 | 12/1934 | Brown | 75/35 |
| 2,048,112 | 7/1936 | Gahl | 75/35 |
| 2,202,174 | 5/1940 | Sullivan | 252/191 |
| 2,213,615 | 9/1940 | Seil | 423/231 |
| 2,528,553 | 11/1950 | Royster | 75/34 |
| 2,551,905 | 5/1951 | Robinson | 423/230 |
| 2,581,135 | 1/1952 | Odell | 423/231 |
| 2,670,946 | 3/1954 | Royster | 266/80 |
| 2,740,706 | 4/1956 | Paull et al. | 75/35 |
| 2,807,535 | 9/1957 | Segre | 266/25 |
| 2,821,471 | 1/1958 | Sellers | 75/26 |
| 2,837,419 | 6/1958 | Sellers et al. | 75/35 |
| 2,967,587 | 1/1961 | Steding et al. | 55/73 |
| 3,193,378 | 7/1965 | Peet | 75/35 |
| 3,375,098 | 3/1968 | Marshall | 75/35 |
| 3,375,099 | 3/1968 | Marshall | 75/35 |
| 3,749,386 | 7/1973 | Beggs et al. | 75/35 |
| 3,816,101 | 6/1974 | Beggs et al. | 75/35 |
| 4,032,120 | 6/1977 | Beggs | 266/159 |
| 4,039,619 | 8/1977 | Steiner | 423/230 |
| 4,087,275 | 5/1978 | Beggs | 75/35 |
| 4,173,465 | 11/1979 | Meissner et al. | 75/35 |
| 4,201,571 | 5/1980 | Scarlett et al. | 75/35 |
| 4,225,340 | 9/1980 | Beggs et al. | 75/35 |
| 4,270,739 | 6/1981 | Ahrendt et al. | 75/35 |
| 4,273,748 | 6/1981 | Takahashi et al. | 423/230 |
| 4,331,470 | 5/1982 | Scarlett et al. | 75/35 |
| 4,333,761 | 6/1982 | Ahrendt et al. | 75/35 |
| 4,351,513 | 9/1982 | Sanzenbacher | 75/35 |
| 4,439,412 | 3/1984 | Behie et al. | 423/648 R |

OTHER PUBLICATIONS

Ironite Products Company, et al., *Ironite Sponge*, 9–82, advertising brochure.

Shumaker et al., "Reaction Rates for Sulfur Fixation with Iron at 1100 to 1275K".

Burklow et al, "Developments in Natural Gas Desulferization", Chemical Engineering Progress (Jun. 1977, pp. 55–58).

Haney et al, "Media for Removing Sulfer from Natural Gas", Chemical Engineering Progress (1970).

Katz et al, *Handbook of Natural Gas Engineering* (McGraw-Hill 1959) pp. 612–624.

Primary Examiner—John Doll
Assistant Examiner—Jeffrey Edwin Russel
Attorney, Agent, or Firm—A. Thomas S. Safford

[57] ABSTRACT

A method for the desulfurization of sour natural gas containing sulfur contaminants wherein the natural gas is first heated to a temperature in the range of 250° C. to 450° C. and then contacted with a bed of sponge iron to remove at least a portion of the sulfur contaminants to form a sweet natural gas.

20 Claims, 1 Drawing Figure

METHOD FOR THE DESULFURIZATION OF HYDROCARBON GAS

This invention relates to a novel and useful method for the effective removal of sulfur compounds from a stream of sulfur-containing hydrocarbon gas such as natural gas. More particularly, sour natural gas is controllably desulfurized to desired low levels of sulfur concentration by contact with a bed of heated sponge iron.

BACKGROUND OF THE INVENTION

In this art it is useful to be conscious of the difference between "sponge iron" and "iron sponge", as these terms are commonly recognized by those skilled in this field. The more commonly known term is "sponge iron", which by more modern and precise terminology (in order to avoid confusion in these terms) is preferably called DRI, or direct reduced iron. Typically, sponge iron may have a metalization of 80% to 95%. Since sponge iron is made by removing oxygen at reducing temperatures below the melting point of the iron-containing material from which it is made, the resulting sponge iron produce (DRI) is typically quite porous with high specific surface.

In contrast, iron oxides, in the form of ore or otherwise, are typically not very porous. Thus to take advantage of the known ability of iron oxide to remove sulfur from sulfur-containing gases, the prior art has developed a porous form of ferric oxide known as "iron sponge". This is attained by creating "mixed oxides" (where finely divided iron oxide is supported on materials of large surface and light weight, typically, wood shavings, wood fluff, or wood chips). Such mixed oxides are also referred to as "iron sponge".

In view of the foregoing, "sponge iron" when used herein, is intended to mean "DRI" (direct reduced iron).

The desulfurization of sulfur-containing gas streams such as sour natural gas is an important expedient in providing commercially viable and valuable sources of process gas or fuel suitable for a multitude of uses. While natural gas is found in many regions of the world, many of the available sources of natural gas frequently additionally contain sulfur contaminants like hydrogen sulfide, carbonyl sulfide and mercaptans.

The term "natural gas" is used herein in its usual meaning as would normally be understood by ones of ordinary skill in the art; as follows: natural gas is a mixture of low molecular weight paraffin series hydrocarbons (methane, ethane, propane, and butane), possibly including with progressively smaller amounts of higher hydrocarbons, and sometimes containing some nitrogen, carbon dioxide, sulfur contaminants (such as hydrogen sulfide, $H_2S$; carbonyl sulfide, COS; and mercaptans), and/or helium; other components, such as hydrogen, would be present, if at all, in only trace amounts (less than 1.0%). Methane usually is the predominant constituent of natural gas, typically, 85% or more.

Depending upon the particular commercial process or end use, the sulfur-containing natural gas stream must be suitably desulfurized to remove substantially all sulfur compounds present therein. Frequently, it is necessary to lower the sulfur concentration to low levels in the range of 0.1 to 0.4 ppm. For example, in processes requiring the use of a catalytic reformer for conversion of a natural gas feed to a reducing gas effective for the reduction of iron ore to sponge iron or for the production of hydrogen, methanol, ammonia, and for other uses, the sulfur content of the natural gas should be less than about 0.2 ppm to avoid sulfur poisoning of the reformer catalyst.

It is noted that the adsorption of sulfur compounds contained in hydrocarbon gas streams by contact with metals or metallic compounds is generally known. Exemplary is U.S. Pat. No. 2,551,905 directed to a process for the desulfurization of a hydrocarbon gas by the countercurrent contact of a sour gas stream with adsorbent ceramic and metal-oxide pellets such as iron oxide at elevated temperatures. In U.S. Pat. No. 3,199,946 a method is disclosed for the removal of hydrogen sulfide from hydrocarbon fuel gases using adsorbent compositions including finely-divided iron metal, moisture and a water soluble alkali metal carbonate, bicarbonate or hydroxide. Further, in U.S. Pat. No. 3,151,973 a method for the production of low sulfur molten iron is disclosed by passing a reducing gas stream through a bed of sponge iron to absorb the sulfur contaminants. Finally, U.S. Pat. No. 3,816,101 discloses the removal of hydrogen sulfide from a stream of process gas at low temperatures.

While the prior art generally recognizes a variety of methods directed to the desulfurization of carbonaceous gases including the use of molecular sieves and metallic compounds such as zinc oxide or even sponge iron, a real need continues to exist for a more economical, efficient and effective method for the desulfurization of natural gas. That is, a method by which a cost-effective, efficient and readily available system can be used to carry out the desulfurization reaction at an acceptable rate of reaction without cracking of components of the natural gas.

OBJECTS OF THE INVENTION

It is accordingly an object of the present invention to provide an ecomonic, efficient and effective process for the desulfurization of natural gas to produce a gas having a very low sulfur concentration.

It is a further object of the invention to provide a process for the desulfurization of natural gas using sponge iron as an effective sulfur absorbent in the desulfurization reaction.

It is still another object of the present invention to provide a process whereby the natural gas is desulfurized in such a manner as to avoid unwanted cracking of components in the natural gas.

DESCRIPTION OF THE INVENTION

By the present invention, sour natural gas is controllably desulfurized by contact with a regulated bed of sponge iron maintained at a temperature in the range of about 250° C. to about 450° C. The temperature of the desulfurization reaction must be carefully controlled to avoid unwanted cracking of the natural gas and to maintain an acceptable desulfurization rate of reaction to insure efficient and effective removal of sulfur to the desired low levels. The upper temperature limit is that minimum temperature when methane or other heavier hydrocarbons which comprise a substantial portion of the natural gas begin to crack. As a result, the reactive bed is poisoned and the methane or other hydrocarbons undergo unwanted chemical conversion.

It has now been discovered that a bed of sponge iron when heated to a temperature in the range of say 250° to 450° C., functions extremely effectively to remove sulfur from natural gas. Further, when operating at a temperature in the range of 300° to 370° C. particularly effective results are achieved. The unexpected advantages attendant the use of sponge iron as a desulfurization agent, include extended active life, lower capital cost and more efficient and effective removal of sulfur compounds from natural gas.

In addition to the process conditions, the characteristics of the sponge iron are important factors in maximizing the efficiency and effectiveness of the desulfurization reaction. More particularly, it has been found that preferred operating conditions and sponge iron specifications are:

| Temperature | 300–370° C. |
|---|---|
| Space Velocity (SCMH of gas/m³ of bed) | 700–2300 |
| Gas Velocity (cm/sec) | 6.0–24.0 |
| Metallization of sponge iron (%) | 80–95 |
| Carbon content of sponge iron (%) | 1.5–2.0 |
| Sponge iron particle size (in.) | ⅛–3/16 |

By the method of this invention, natural gas comprised primarily of methane and containing sulfur concentrations as high as 700 ppm can be efficiently desulfurized to a sulfur concentration of 0.10 ppm by heating the natural gas stream to a temperature in the range of 250°–450° C. and then passing the heated gas stream over a fixed bed of selected sponge iron particles.

It has been determined that the heating of the sour gas stream to a temperature within the prescribed temperature range favors both the kinetics of the desulfurization reaction wherein sulfur is adsorbed by the sponge iron, and avoids the undesirable cracking of methane or other heavier hydrocarbons known to occur at temperatures in excess of 450° C. as illustrated by the following general reaction:

$$C_nH_{2n+2} \rightarrow nC + (n+1)H_2$$

The rate of increase in reactor space velocity as a function of temperature improves significantly at a temperature of 250° C. and is shown in FIG. 1. Reactor space velocity is defined in this process as volume of gas desulfurized per unit of time measured at standard conditions divided by volume of reactor. Therefore, it is clear that at a constant flow rate a steep increase in space velocity is proportional to a decrease in required reactor volume. As illustrated in FIG. 1, values of reactor space velocity for temperatures between 250° C. and 370° C. increase from 240–2,250 (std m³ gas per hr/m³ bed).

These high space velocity values far exceed the recommended space velocities for the traditional iron-oxide desulfurization process such as disclosed in the literature (e.g., Maddox, *Gas and Liquid Sweetening*, edited by Campbell Petroleum Series, Chapter 7 (1977). Further, this unexpected advance in the art of natural gas desulfurization not only exceeds the purification achieved by Fujita et al. in the use of an iron metal-alkaline composition (cf. U.S. Pat. No. 3,199,946), but also achieves such superior results in a more efficient and economical manner.

It must be appreciated that the desulfurization of natural gas comprised primarily of methane is distinguishable over those prior art methods in which sponge iron is used in the desulfurization of process gas. The presence of CO and H₂ in such gases necessarily inhibits the hydrogen sulfide and carbonyl sulfide desulfurization reactions shown below.

$$Fe + H_2S \rightarrow FeS + H_2$$

$$Fe + COS \rightarrow FeS + CO$$

Therefore, the present invention is particularly useful for desulfurization of natural gas feedstocks having high concentrations of carbonyl sulfide which cannot be effectively treated by adsorbents such as activated carbon, molecular sieves, and other absorbents as Zinc Oxide.

Finally, by the process of the present invention only a short mass-transfer zone in the fixed bed of sponge iron is required the effective length of which is largely independent of increases in the sulfur level of the inlet gas. In this aspect the present invention is far superior to moving bed desulfurization processes disclosed in the art.

From the foregoing description it is apparent that the disclosed process for desulfurization of natural gas at a predetermined temperature over a fixed bed of sponge iron represents a new and useful improvement over the prior desulfurization art.

Although certain embodiments of the invention have been described, variation of such embodiments and other aspects of this invention will be readily ascertained by those skilled in the art, subject only to the limitations of the following claims:

We claim:

1. A method for the desulfurization of sour natural gas containing sulfur contaminants naturally occurring in natural gas which comprises heating the sour natural gas to a desulfurization reaction temperature in the range of 250° C. to 450° C., contacting the heated sour natural gas with a bed of sponge iron to remove at least a portion of the sulfur contaminants to form a sweet natural gas.

2. The method of claim 1 wherein the sweet natural gas contains no more than 0.4 ppm of sulfur contaminants.

3. The method of claim 1 wherein the sweet natural gas contains no more than 0.1 ppm of sulfur contaminants.

4. The method of claim 1 wherein the desulfurization reaction temperature is in the range of 300° C. to 370° C.

5. The method of claim 1 wherein the sponge iron has a metallization of at least 80% and a carbon content of at least 1.5%.

6. The method of claim 1 wherein the sour natural gas contains up to 700 ppm of sulfur contaminants.

7. The method of claim 6 wherein the sponge iron has a particle size in the range of ⅛ to 3/16 inches.

8. A method for the desulfurization of sour natural gas containing sulfur contaminants naturally occurring in natural gas, which method comprises heating the natural gas to a desulfurization reaction temperature in the range of 250° C. to 450° C., feeding said natural gas to a reaction vessel containing a bed of sponge iron at a reactor space velocity of 700 to 2300 SCMH/m³ relative to the bed of sponge iron so as to contact the heated sour natural gas with said sponge iron to remove from the gas at least a portion of the sulfur contaminants to form a sweet natural gas.

9. The method of claim 8 wherein the sweet natural gas contains no more than 0.4 ppm of sulfur contaminants.

10. The method of claim 8 wherein the sweet natural gas contains no more than 0.1 ppm of sulfur contaminants and said bed of sponge iron is fixed.

11. The method of claim 8 wherein the desulfurization reaction temperature is in the range of 300° C. to 370° C.

12. The method of claim 8 wherein the sponge iron has a metallization of at least 80% and a carbon content of at least 1.5%.

13. The method of claim 12 wherein the sponge iron has a particle size in the range of ⅛ to 3/16 inches.

14. The method of claim 8 wherein the sour natural gas contains up to 700 ppm of sulfur contaminants.

15. A method for the desulfurization of sour natural gas containing at least COS as a sulfur contaminant thereof, which comprises heating the sour natural gas to a desulfurization reaction temperature in the range of 250° C. to 450° C., contacting the heated sour natural gas with a bed containing an amount of sponge iron effective to remove at least a portion of the COS to form a sweet natural gas.

16. The method of claim 15, wherein the sponge iron has a metallization of at least 80% and a carbon content of at least 1.5%.

17. The method of claim 16, wherein the sweet natural gas contains no more than 0.4 ppm of sulfur contaminants; and further comprises feeding said sour natural gas to said bed of sponge iron at a space velocity of 700 to 2300 SCMH/m$^3$ of said bed.

18. The method of claim 17, wherein the desulfurization reaction temperature is in the range of 300° C. to 370° C.

19. The method of claim 17, wherein the sponge iron has a particular size in the range of ⅛ to 3/16 inches; the sweet natural gas contains no more than 0.1 ppm of sulfur contaminants; and the sour natural gas contains up to 700 ppm of sulfur contaminants.

20. The method of claim 15, wherein the COS content of said sour natural gas is in excess of that which can be effectively treated by activated carbon, molecular sieves, or zinc oxide.

* * * * *